(12) United States Patent
Omura et al.

(10) Patent No.: US 6,835,747 B1
(45) Date of Patent: Dec. 28, 2004

(54) FT-0554A SUBSTANCES AND PROCESS FOR THE PREPARATION THEREOF

(75) Inventors: Satoshi Omura, Tokyo (JP); Kazuro Shiomi, Tokyo (JP); Tohru Nagamitsu, Kanagawa (JP); Toshiaki Sunazuka, Chiba (JP); Yuzuru Iwai, Chiba (JP)

(73) Assignee: The Kitasato Institute, Tokyo (JP)

( * ) Notice: Subject to any disclaimer, the term of this patent is extended or adjusted under 35 U.S.C. 154(b) by 0 days.

(21) Appl. No.: 10/343,995

(22) PCT Filed: Aug. 22, 2000

(86) PCT No.: PCT/JP00/05613

§ 371 (c)(1),
(2), (4) Date: Jul. 28, 2003

(87) PCT Pub. No.: WO02/16336

PCT Pub. Date: Feb. 28, 2002

(51) Int. Cl.$^7$ .................... A61K 31/341; C07D 307/20
(52) U.S. Cl. ..................... 514/473; 549/313; 514/473
(58) Field of Search .......................... 514/473; 549/313

(56) References Cited

U.S. PATENT DOCUMENTS 6,486,197 B1 * 11/2002 Omura et al. .............. 514/456

FOREIGN PATENT DOCUMENTS

WO    WO 99/244/39    5/1999

OTHER PUBLICATIONS

Biochimica et Biophysica Acta, Schilling et al., "Amine oxidases from Aspergillus niger: identification of a novel flavin–dependent enzyme", 1994, pp. 529–537.

(List continued on next page.)

*Primary Examiner*—Joseph K. McKane
*Assistant Examiner*—Janet L Coppins

(74) *Attorney, Agent, or Firm*—Young & Thompson

(57) ABSTRACT

The present invention relates to obtain novel FT-0554A substance useful for infectious disease of parasite, especially helminth and more particularly relates to the novel FT-0554A substance represented by the following formula [I]

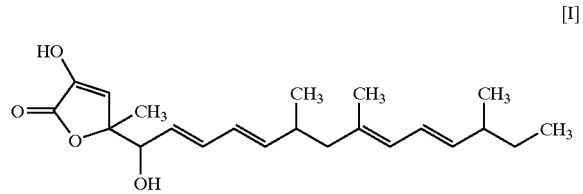

or the tautomer thereof represented by the formula [II]

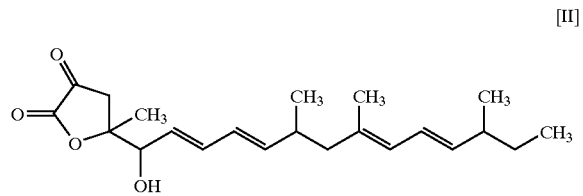

obtained by treating FT-0554 substance represented by the formula [II]

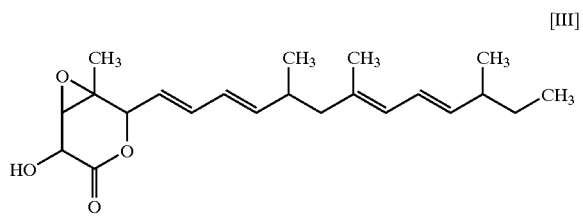

under alkaline condition.

6 Claims, 1 Drawing Sheet

OTHER PUBLICATIONS

Eur. J. Biochem., Inoue et al., "Metabolism of 2-oxoaldehyde in mold", 1988, pp. 213–218.

Abstract, Satoshi Omura et al., "Novel substance FT–0554 and process for producing the same".

* cited by examiner

FT-0554A SUBSTANCES AND PROCESS FOR THE PREPARATION THEREOF

BACKGROUND OF THE INVENTION

(1) Field of the Invention

This invention relates to novel FT-0554A substance useful for treatment for infection of parasite, especially helminth, and its production.

(2) Description of the Related Art

Parasitosis is reducing as a result of improvement in sanitary conditions and progress of anthelmintics. Recently, however, the import parasitosis, zoonotic parasitosis, opportunistic parasitosis and parasitosis originated from perishable foods are prevailing and become crucial problems. Further the parasitosis produces large economical burdens in the stock-farming and agriculture. For infection of helminth in the parasite, at present, avermectins, mebendazole, praziquantel, and others are used for treatment of helminth.

SUMMARY OF THE INVENTION

Anthelmintics used at present, such as avermectins, mebendazole and praziquantel, are not always sufficient for satisfactory in efficacy and toxicity, in addition, helminth which acquired resistance to the conventional anthelmintics is increasing, consequently novel drugs are strongly required.

We have studied NADH-fumarate reductase, which was one of the promising targets against anthelmintics, in the electron transport system of the helminth, and explored for the inhibitor of the NADH-fumarate reductase from the microbial culture. As a result, we have found that FT-0554 substance produced by a strain belonging, to genus *Aspergillus, Aspergillus niger* had NADH-fumarate reductase inhibitory activity, and had made international patent application (international publication no. WO99/24439).

The above described *Aspergillus niger* is described in Boris Schilling et al., "Amine oxidases from *Aspergillus niger*:identification of a novel flavin-dependent enzyme", Biochimica et Biophysica Acta Vol. 1243 (1995) p. 529–537, and Yoshiharu Inoue et al., "Metabolism of 2-oxoaldehyde in mold. Purification and characterization of two methylglyoxal reductases from *Aspergillus niger*", Eur. J. Biochem Vol. 171 (1988) p. 213–218.

As a result of our continued studies, we have found that novel FT-0554A substance derived from FT-0554 substance had also equivalent level of inhibitory activity of NADH-fumarate reductase, and completed the present invention.

Namely, the present invention relates to FT-0554A substance represented by the formula [I]:

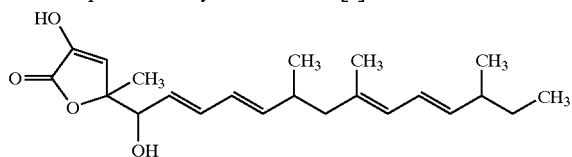

or its tautomer of the formula [II]:

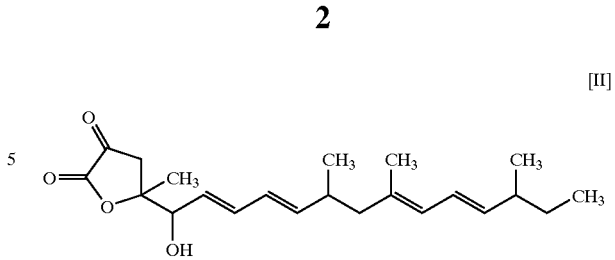

Further, the present invention relates to FT-0554A substance having the following physicochemical properties.

(1) Nature: white powder or amorphous
(2) Molecular weight: 383.2201 (M+Na, high resolution fast atom bombardment mass spectrometry)
(3) Molecular formula: $C_{22}H_{32}O_4$
(4) Melting point: 101–103° C.
(5) Specific rotation: $[\alpha]_D^{26}$=+4.6° (c=1, chloroform)
(6) IR absorption maximum (KBr Tab): As shown in FIG. 1, maximum absorption at 3375, 2960, 2926, 1755, 1738, 1660, 1456, 1261, 1074, 1024, and 800 $cm^{-1}$
(7) Solubility in solvent: soluble in chloroform and ethyl acetate; insoluble in water and n-hexane,
(8) Color reaction: positive for phosphomolybdic acid reagent.

Further, the present invention relates to a process for production of FT-0554A substance of the formula [I]

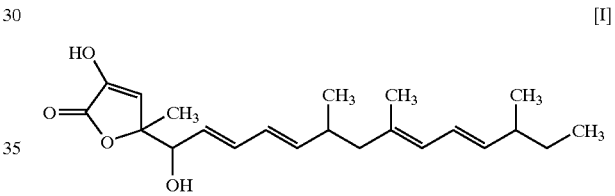

or its tautomer of the formula [II]

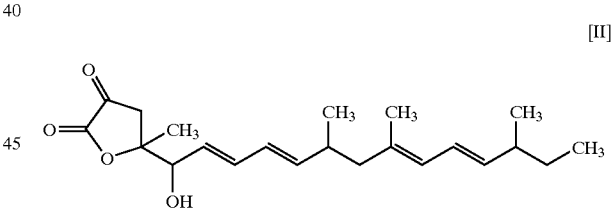

wherein FT-0554 substance represented by the formula [III]

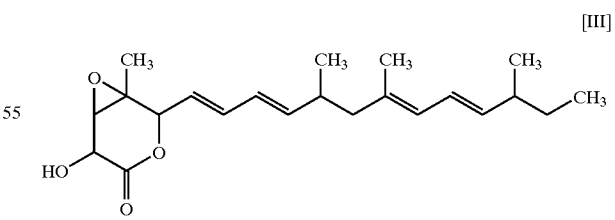

is treated by alkali.

The present invention further relates to NADH-fumarate reductase inhibitor comprising FT-0554A substance as an active ingredient.

Furthermore, the present invention relates to antihelminthic agent comprising FT-0554A substance as an active ingredient.

Detailes physicochemical properties of FT-0554A substance of the present invention are as follows.

(1) Nature: white powder or amorphous
(2) Molecular weight: 383.2201 (M+Na, high resolution fast atom bombardment mass spectrometry)
(3) Molecular formula: $C_{22}H_{32}O_4$
(4) Melting point: 101–103° C.
(5) Specific rotation: $[\alpha]_D^{26}=+4.60°$ (c=1, chloroform)
(6) IR absorption maximum (KBr Tab): As shown in FIG. 1, maximum absorption at 3375, 2960, 2926, 1755, 1738, 1660, 1456, 1261, 1074, 1024, and 800 $cm^{-1}$
(7) $^1$H-proton Nuclear Magnetic Resonance spectrum: chemical shift of FT-0554A substance [I] in deuteroacetone (ppm) is as follows.
s: singlet, d: doublet, t: triplet, q: quartet, m: multiplet, br: broad, H: number of proton, J: coupling constant (Hz)

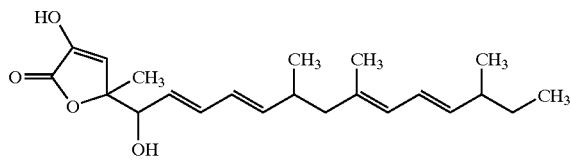

[I]

6.17 s (1H, H-3), 6.25 dd (1H, J=10.5, 15.1, H-7), 6.18 dd (1H, J=10.7, 15.1, H-14), 6.02 dd (1H, J=10.5, 15.4, H-8), 5.74 d (1H, J=10.7, H-13), 5.61 dd (1H, J=7.2, 15.4, H-9), 5.58 dd (1H, J=7.2, 15.1, H-6), 5.39 dd (1H, J=8.0, 15.1, H-15), 4.32 br.d (1H, J=4.0, 5-OH), 4.08 m (1H, H-5), 2.40 m (1H, H-10), 2.05 m (1H, Ha-11), 2.01 m (1H, H-16), 1.93 m (1H, Hb-11), 1.67 s (3H, 12-$CH_3$), 1.32 s (3H, 4-$CH_3$), 1.25 m (2H, $H_2$-17), 0.93 d (3H, J=6.6, 16-$CH_3$), 0.91 d (3H, J=6.9, 10-$CH_3$), 0.80 t (3H, J=7.4, $H_3$-18)

(8) $^1$H-proton Nuclear Magnetic Resonance Spectrum: chemical shift of FT-0554A substance [II] in deuteroacetone (ppm) is as follows.
s: singlet, d: doublet, t: triplet, q: quartet, m: multiplet, br: broad, H: number of proton, J: coupling constant (Hz)

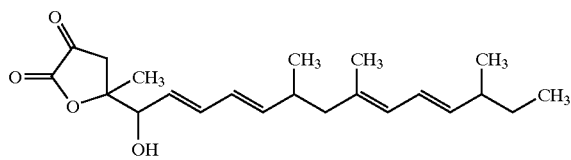

[II]

6.34 dd (1H, J=10.5, 15.1, H-7), 6.18 dd (1H, J=10.7, 15.1, H-14), 6.05 dd (1H, J=10.5, 15.4, H-8), 5.74 d (1H, J=10.7, H-13), 5.67 dd (1H, J=7.2, 15.4, H-9), 5.61 dd (1H, J=7.2, 15.1, H-6), 5.39 dd (1H, J=8.0, 15.1, H-15), 5.11 br.d (1H, J=3.6, 5-OH), 4.22 m (1H, H-5), 2.88 d (1H, J=18.7, Ha-3), 2.55 d (1H, J=18.7, Hb-3), 2.40 m (1H, H-10), 2.05 m (1H, Ha-11), 2.01 m (1H, H-16), 1.93 m (1H, Hb-11) 1.67 s (3H, 12-$CH_3$), 1.48 s (3H, 4-$CH_3$), 1.25 m (2H, $H_2$-17), 0.93 d (3H, J=6.6, 16-$CH_3$), 0.91 d (3H, J=6.9, 10-$CH_3$), 0.80 t (3H, J=7.4, $H_3$-18)

(9) $^{13}$C-Nuclear Magnetic Resonance spectrum: chemical shift of FT-0554A substance [I] in deuteroacetone (ppm) is as follows.
s: singlet, d; doublet, t: triplet, q: quartet

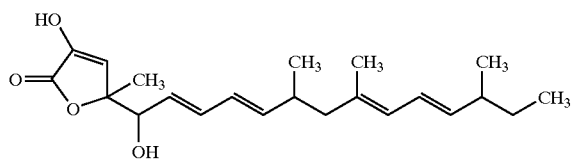

[I]

169.0 s (C-1), 141.4 d (C-9), 138.8 d (C-15), 134.74 s (C-12), 133.8 d (C-7), 130.0 d (C-6), 128.6 d (C-8), 127.7 d (C-13), 125.9 d (C-14), 121.5 d (C-3), 86.2 s (C-4), 76.6 d (C-5), 48.1 t (C-11), 39.3 d (C-16), 35.6 d (C-10), 30.4 t (C-17), 21.3 q (4-$CH_3$), 20.5 q (16-$CH_3$), 20.1 q (10-$CH_3$), 16.5 q (12-$CH_3$), 12.0 q (C-18), C2 cannot be identified.

(10) $^{13}$C-Nuclear Magnetic Resonance spectrum: chemical shift of FT-0554A substance [II] in deuteroacetone (ppm) is as follows.
s: singlet, d: doublet, t: triplet, q: quartet

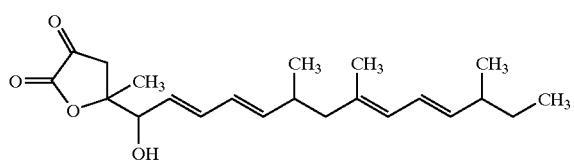

[II]

193.7 s (C-2), 161.5 s (C-1), 142.4 d (C-9), 138.9 d (C-15), 135.0 d (C-7), 134.66 s (C-12), 128.7 d (C-6), 128.3 d (C-8), 127.6 d (C-13) 125.9 d (C-14), 84.9 s (C-4), 77.0 d (C-5), 48.2 t (C-11), 40.6 d (C-3), 39.3 d (C-16), 35.5 d (C-10), 30.4 t (C-17), 23.3 q (4-$CH_3$), 20.5 q (16-$CH_3$), 20.0 q (10-$CH_3$), 16.5 q (12-$CH_3$), 12.0 q (C-18)

(11) Solubility in solvent: soluble in chloroform and ethyl acetate; hardly soluble in water and n hexane
(12) Color reaction: positive for phosphomolybdic acid reagent.

As a result of detailed examination of physico-chemical properties and spectra data of FT-0554A substance, FT-0554A substance is determined as the following chemical structure [I]:

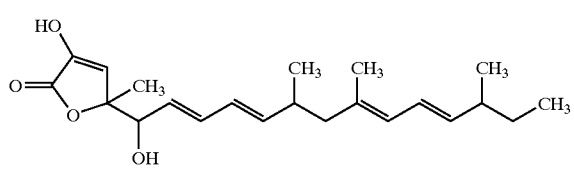

[I]

or its tautomer of the formula [II]:

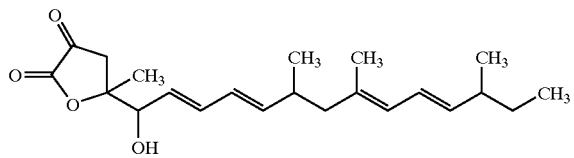

[II]

As shown in the above, physico-chemical properties of FT-0554A substance are described in detail, however no compound having identical properties has been reported. Consequently, FT-0554A substance is defined as novel substance.

Next, the production of FT-0554A substance of the present invention from FT-0554 substance is explained concretely.

A microorganism having FT-0554 substance producing activity belonging to *Aspergillus, Aspergillus niger* FT-0554 FERM BP-6443, disclosed in the international publication no. WO99/24439 is cultured in the medium, to accumulate FT-0554 substance in the cultured medium and to isolate FT-0554 substance represented by the following formula [III] from the cultured medium.

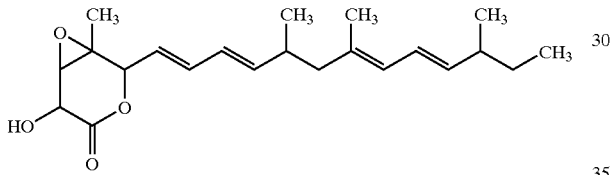

[III]

The thus obtained FT-0554 substance is treated under alkaline condition to produce FT-0554A substance of the present invention.

Namely, FT-0554 substance is dissolved in the conventional organic solvent, for example, alcohol such as methanol, ethanol, etc., ether such as diethyl ether, dimethyl sulfoxide and chloroform, and basic compound such as potassium carbonate, sodium carbonate, potassium hydrogen carbonate, sodium hydrogen carbonate, sodium methoxide, sodium hydride, sodium hydroxide, potassium hydroxide and anmmonium is added to generate FT-0554A substance.

Purification and isolation of the substance from the reaction mixture can be performed by the conventional methods used for purification of the common lipophilic organic compound, for example, extraction with water immiscible organic solvent such as ethyl acetate, various chromatographic methods such as absorption chromatography, gel-filtration chromatography, scratching from thin layer chromatography, centrifugal counter-current chromatography, and high performance liquid chromatography, and precipitation from slightly soluble solvent, with combination thereof or repeating these process, as a result, purified FT-0554A substance can be obtained.

NADH-fumarate reductase inhibitory activity of FT-0554A substance of the present invention is explained as follows.

Muscles of *Ascaris suum* were homogenized in 120 mM sodium phosphate solution (pH 7.0) and centrifuged at 3000×g for 10 minutes to collect the supernatant solution. The supernatant was further centrifuged at 10000×g for 20 minutes to collect the precipitate. The precipitate was suspended in 120 mM sodium phosphate solution (pH 7.0) to obtain mitochondorial fraction.

After 10 µl of test sample dissolved in 50% dimethyl sulfoxide solution was added into 96 wells microplate, 80 µl of 120 mM sodium phosphate solution (pH 7.0) containing 0.35 mM NADH, 7.2 mM disodium fumarate and 18 mg/ml bovine serum albumin was added thereto, and pre-incubated in the microplate reader ELX808 (Bio-Teck Industries Co.) at 37° C. for 5 minutes. Mithochondrial fraction of *Ascaris suum* 10 µl (protein content 0.3 mg) was added therein and incubated at 37° C. for 10 minutes. Absorption of NADH at 340 nm was measured every 15 seconds.

As a result of quantitative measurement of NADH-fumarate reductase activity shown by decrease in the slope of absorbancy at 340 nm, 50% inhibition of NADH-fumarate reductase activity were obtained at 0.4 µM of FT-0554A substance. Consequently, FT-0554A substance can be expected to use as drug for treatment or prevention of helminthiasis.

DETAILED DESCRIPTION OF PREFERRED EMBODIMENT

Figure 1:
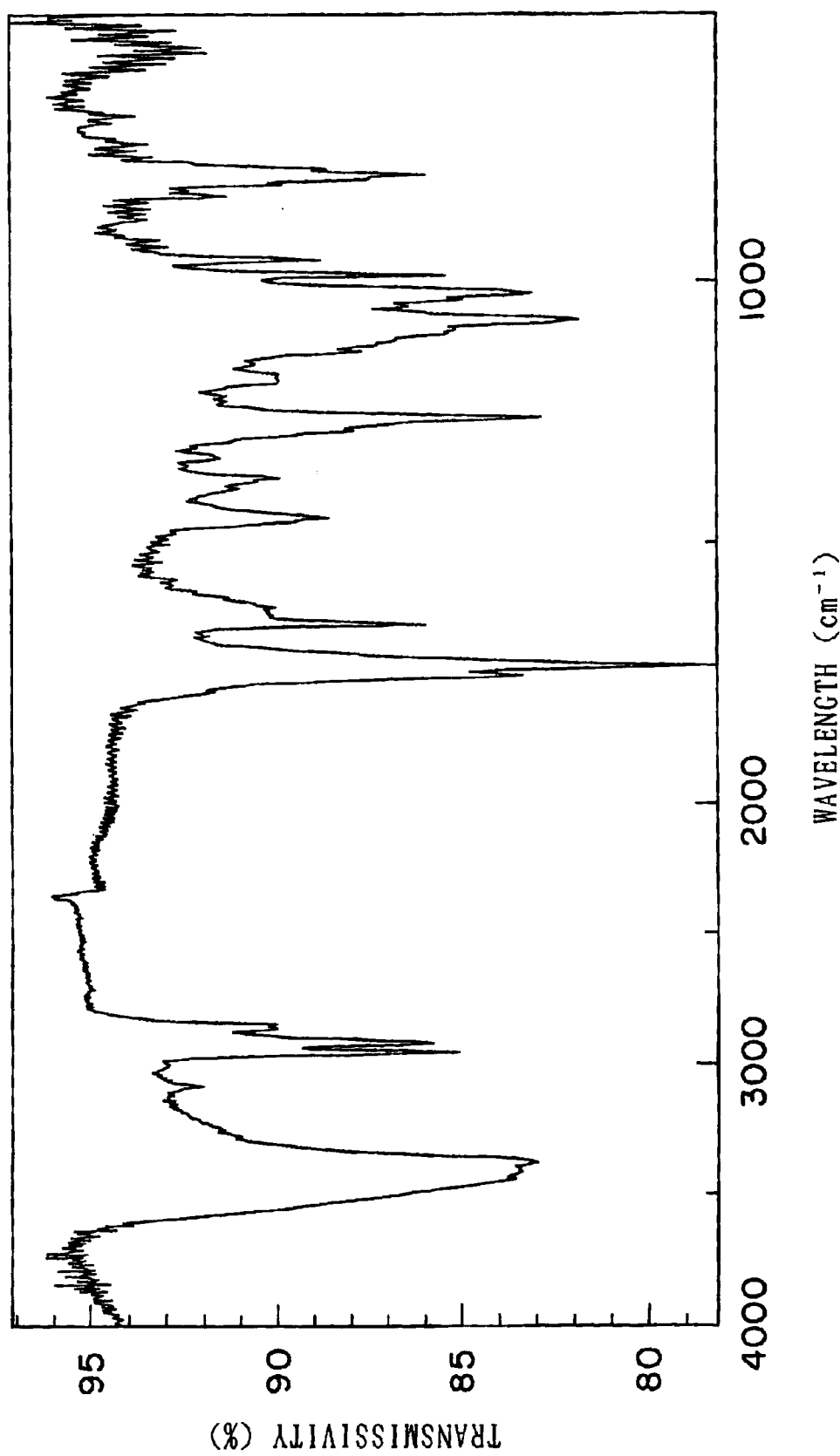
FIG. 1 shows IR spectrum of FT-0554A substance of the present invention (KBr Tab).

The following example illustrates the present invention, but is not construed to limit the invention.

EXAMPLE

FT-0554A substance 10.0 mg was dissolved in methanol 280 µl, added calcium carbonate 2.0 mg therein and stirred. After kept at room temperature for 30 minutes, the reaction mixture was diluted by adding ethyl acetate, added saturated sodium chloride and treated by the extraction operation. Organic layer was separated, dried by adding, anhydrous sodium sulfate, and concentrated in vacuo to obtain FT-0554A substance 9.3 mg, as white powder.

EFFECT OF THE INVENTION

As explained hereinabove, the present invention provides FT-0554A substance or the process for production of FT-0554A substance from FT-0554 substance, and the thus obtained FT-0554A substance is expected to be a satisfactory and useful medicament for treatment of parasitosis.

What is claimed is:
1. A compound represented by formula [I]

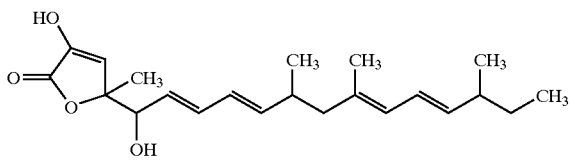

[I]

or the tautomer thereof of formula [II]

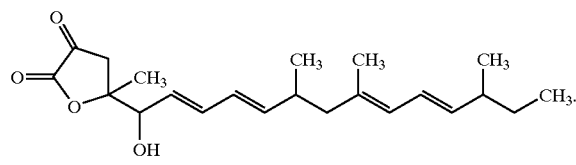

[II]

2. A composition comprising a compound according to claim 1 having the following physiochemical properties:
   (1) Nature: white powder or amorphous
   (2) Molecular weight: 383.2201 (M+Na, high resolution fast atom bombardment mass spectrometry)
   (3) Molecular formula: $C_{22}H_{32}O_4$
   (4) Melting point: 101–103° C.
   (5) Specific rotation: $[\alpha]_n^{26}=+4.6°$ (c=1, chloroform)
   (6) IR absorption maximum (KBr Tab): As shown in FIG. 1, maximum absorption at 3375, 2960, 2926, 1755, 1738, 1660, 1456, 1261, 1074, 1024, and 800 $cm^{-1}$
   (7) solubility in solvent: soluble in chloroform and ethyl acetate, hardly soluble in water and n-hexane, and
   (8) Color reaction: positive for phosphomolybdic acid reagent, and an inert carrier.

3. A process for production of a composition comprising a compound of formula [I]

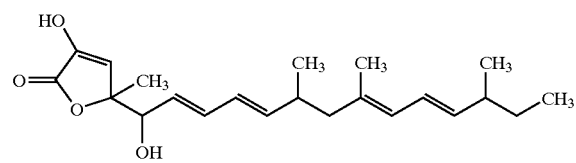

[I]

or the tautomer thereof represented by formula [II]

[II]

comprising creating a compound represented by formula [III]

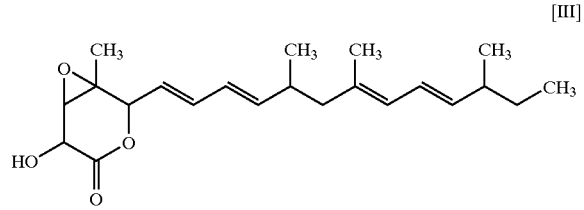

[III]

under alkaline condition.

4. A method of inhibiting NADH-fumarate reductase in vitro comprising administering to a mitochondria suspension an NADH-fumarate reductase inhibiting effective amount of a composition containing a compound of formula

[I]

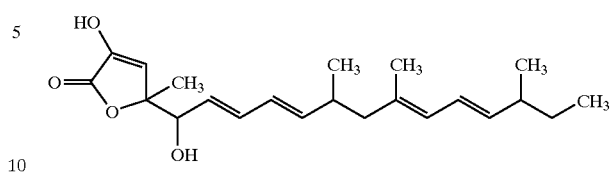

or the tautomer thereof of formula [II]

[II]

5. A method of treating helminthiasis in a human or an animal or a human or animal at risk of contracting helminthiasis, comprising administering an effective amount of a composition to said human or animal and wherein said composition contains a compound of formula [I]

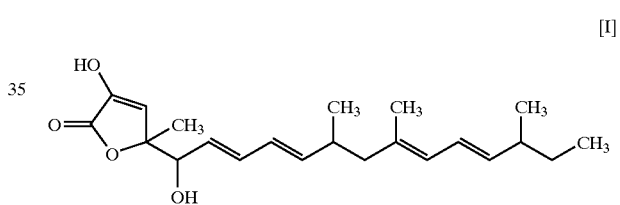

[I]

or the tautomer thereof of formula [II]

[II]

6. A method for producing a composition comprising a compound of formula [I]

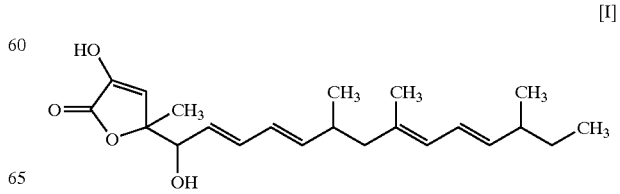

[I]

or the tautomer thereof of formula [II]

[II]

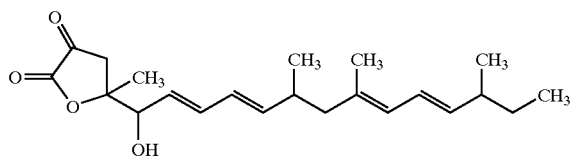

said method comprising culturing in medium microorganism *Aspergillus niger* FT-0554 which produces a compound represented by formula [III]

[III]

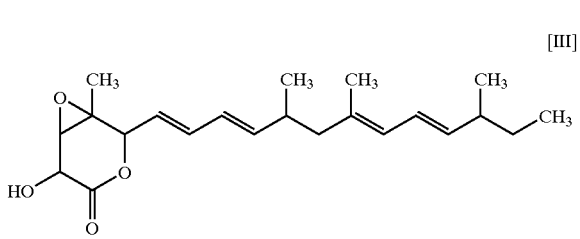

isolating the compound represented by formula [III] from the cultured medium, and treating the compound under alkaline conditions to produce a compound of formula [I]

[I]

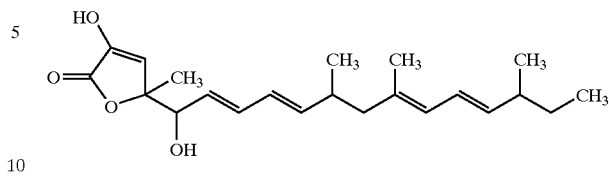

or the tautomer thereof of formula [II]

[II]

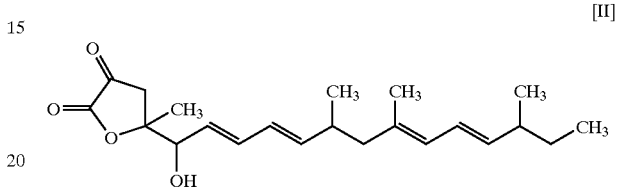

and wherein compound I or compound II are added to said composition.

* * * * *